United States Patent [19]

Enomoto et al.

[11] Patent Number: 4,946,961
[45] Date of Patent: Aug. 7, 1990

[54] BENZOTHIAZOLONES, AND THEIR PRODUCTION AND USE

[75] Inventors: Masayuki Enomoto, Takarazuka; Eiki Nagano, Tokyo; Toru Haga, Takarazuka; Kouichi Morita; Ryo Sato, both of Toyonaka, all of Japan

[73] Assignee: Sumitomo Chemical Company, Limited, Osaka, Japan

[21] Appl. No.: 373,197

[22] Filed: Jun. 29, 1989

Related U.S. Application Data

[62] Division of Ser. No. 131,742, Dec. 11, 1987.

[30] Foreign Application Priority Data

Dec. 11, 1986 [JP] Japan .............................. 61-296041

[51] Int. Cl.$^5$ .......................................... C07D 417/14
[52] U.S. Cl. ...................................................... 548/159
[58] Field of Search ......................................... 548/159

[56] References Cited

U.S. PATENT DOCUMENTS

| 4,075,216 | 2/1978 | D'Amico .................................. 71/90 |
| 4,720,297 | 1/1988 | Haga et al. ............................. 71/90 |
| 4,831,150 | 5/1989 | Haga ...................................... 548/159 |

FOREIGN PATENT DOCUMENTS

| A142769 | 11/1984 | European Pat. Off. .............. 548/1 |
| A218972 | 4/1987 | European Pat. Off. . |

*Primary Examiner*—Robert Gerstl
*Attorney, Agent, or Firm*—Birch, Stewart, Kolasch & Birch

[57] ABSTRACT

A compound of the formula:

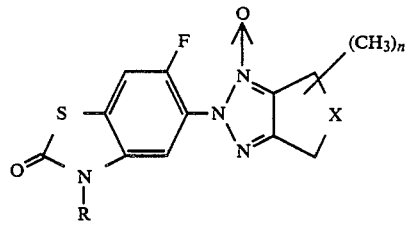

wherein R is a $C_1$–$C_5$ alkyl group, a $C_3$–$C_4$ alkenyl group, a $C_3$–$C_4$ alkynyl group, a $C_1$–$C_2$ alkoxy($C_1$–$C_2$)alkyl group, a $C_1$–$C_2$ alkylthio($C_1$–$C_2$)alkyl group or a mono- or polyfluoro($C_1$–$C_3$)alkyl group, X is a $C_1$–$C_4$ alkylene group which may be substituted with at least one methyl or a —$OCH_2$— group and n is an integer of 0, 1 or 2, which is useful as a herbicide.

1 Claim, No Drawings

BENZOTHIAZOLONES, AND THEIR PRODUCTION AND USE

This application is a divisional of copending application Ser. No. 07/131,742 filed on Dec. 11, 1987.

The present invention relates to benzothiazolones, and their production and use. More particularly, the invention relates to novel benzothiazolones, a process for producing them, and their use as herbicides.

Certain benzothiazolone derivatives such as 4-chloro2,3-dihydro-2-oxobenzothiazol-3-ylacetic acid (benazolin) [Herbicide Handbook of the Weed Science Society of America, 5th Ed., p. 40 (1983)] are known to be effective as herbicides. However, their herbicidal activity is not necessarily satisfactory.

It has now been found that the benzothiazolones of the formula:

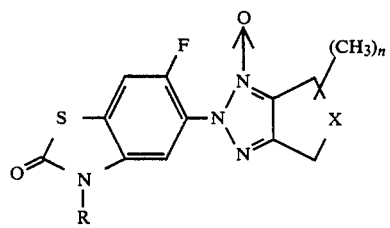

wherein R is a $C_1-C_5$ alkyl group, a $C_3-C_4$ alkenyl group, a $C_3-C_4$ alkynyl group, a $C_1-C_2$ alkoxy($C_1-C_2$)alkyl group, a $C_1-C_2$ alkylthio($C_1-C_2$)alkyl group or a mono- or polyfluoro($C_1-C_3$)alkyl group, X is a $C_1-C_4$ alkylene group which may be substituted with at least one methyl or a —OCH$_2$— group and n is an integer of 0, 1 or 2 show a high herbicidal activity against a wide variety of weeds including broad-leaved weeds, Graminaceous weeds and Commelinaceous weeds in agricultural plowed fields by foliar or soil treatments without producing any material phytotoxicity on various agricultural crops such as corn, wheat, rice plant, soybean, cotton and sugarbeet. Examples of the broad-leaved weeds include wild buckwheat (*Polygonum convolvulus*), pale smartweed (*Polygonum lapathifolium*), common purslane (*Portulaca oleracea*), common chickweed (*Stellaria media*), common lambsquarters (*Chenopodium album*), redroot pigweed (*Amaranthus retroflexus*), radish (*Raphanus sativus*), wild mustard (*Sinapis arvensis*), shepherdspurse (*Capsella bursa-pastoris*), hemp sesbania (*Sesbania exaltata*), sicklepod (*Cassia obtusifolia*), velvetleaf (*Abutilon theophrasti*), prickly sida (*Sida spinosa*), field pansy (*Viola arvensis*), catchweed bedstraw (*Galium aparine*), ivy-leaf morningglory (*Ipomoea hederacea*), tall morningglory (*Ipomoea purpurea*), field bindweed (*Convolvulus arvensis*), jimsonweed (*Datura stramonium*), black nightshade (*Solanum nigrum*), persian speedwell (*Veronica persica*), common cocklebur (*Xanthium pensylvanicum*), common sunflower (*Helianthus annuus*), scentless chamomile (*Matricaria perforata*), corn marigold (*Chrysanthemum segetum*), etc. Examples of Graminaceous weeds include Japanese millet (*Echinochloa frumentacea*), barnyardgrass (*Echinochloa crus-galli*), green foxtail (*Setaria viridis*), large crabgrass (*Digitaria sanguinalis*), annual bluegrass (*Poa annua*), blackgrass (*Alopecurus myosuroides*), oats (*Avena sativa*), wild oats (*Avena fatua*), johnsongrass (*Sorghum halepense*), etc. Examples of the Commelinaceous weeds include asiatic dayflower (*Commelina communis*), etc.

The benzothiazolones (I) of the invention are also effective in exterminating paddy field weeds including Graminaceous weeds such as barnyardgrass (*Echinochloa oryzicola*), broad-leaved weeds such as common falsepimpernel (*Lindernia procumbens*), indian toothcup (*Rotala indica*) and waterwort (*Elatine triandra*), Cyperaceous weeds such as hardstem bulrush (*Scirpur juncoides*), needle spikerush (*Eleocharis acicularis*) and and water nutgrass (*Cyperus serotinus*), and others such as monochoria (*Monochoria vaginalis*) and arrowhead (*Sagittaria pygmaea*) without producing any phytotoxicity to rice plants on flooding treatment.

Among the benzothiazolones (I), preferred are those wherein R is a $C_2-C_4$ alkyl group, a $C_3-C_4$ alkenyl group, a $C_3-C_4$ alkynyl group or a $C_1-C_2$ alkoxymethyl group, X is a $C_1-C_2$ alkylene group or a —OCH$_2$— group and n is 0. More preferred are those wherein X is a $C_1-C_2$ alkylene group. Still more preferred are those wherein R is a $C_2-C_4$ alkyl group, a $C_3-C_4$ alkenyl group or a $C_3-C_4$ alkynyl group, X is a $C_1-C_2$ alkylene group and n is 0. The most preferred are those wherein X is a $C_2$ alkylene group. Typical examples of the preferred compounds are 2-[6-fluoro-3(1-methylethyl)-2(3H)-benzothiazolon-5-yl]-4,5,6,7-tetrahydro-2H-benzotriazole-1-oxide, 2-[6-fluoro-3-(2-propenyl)2(3H)-benzothiazolon-5-yl]-4,5,6,7-tetrahydro-2H-benzotriazole-1-oxide, 2-[6-fluoro-3-(2-propynyl)-2(3H)-benzothiazolon-5-yl]-4,5,6,7-tetrahydro-2H-benzotriazole-1-oxide, etc.

The benzothiazolones (I) of the present invention are prepared by reacting a compound of the formula:

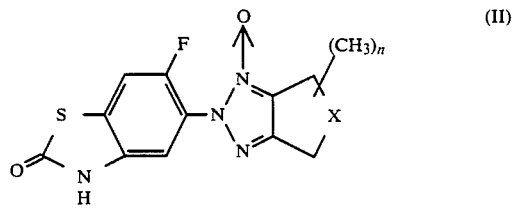

wherein X and n are each as defined above with a compound of the formula:

wherein R is as defined above and Y is an acid-forming reactive group such as a chlorine atom, a bromine atom, an iodine atom, a methanesulfonyl group or a p-toluenesulfonyl group, usually in a solvent at a temperature of about 0° to 120° C. for a period of about 0.5 to 24 hours in the presence of a base.

The compound (III) and the base may be respectively used in amounts of about 1.0 to 1.5 equivalents and of about 1.0 to 1.5 equivalents to the compound (II). As the solvent, there may be used aromatic hydrocarbons (e.g. benzene, toluene, xylene), ethers (e.g. dioxane, tetrahydrofuran, diethyleneglycol dimethyl ether), nitriles (e.g. acetonitrile, isobutylonitrile), acid amides (e.g. formamide, N,N-dimethylformamide, acetamide), sulfur compounds (e.g. dimethylsulfoxide, sulphorane), water, etc. These may be used solely or in combination. Examples of the base are inorganic bases (e.g. sodium hydroxide, potassium hydroxide, sodium carbonate, potassium carbonate, sodium hydride), etc.

After completion of the reaction, the reaction mixture is subjected to an ordinary post-treatment such as extraction with an organic solvent and concentration. If desired, any conventional purification procedure such as chromatography or recrystallization may be adopted.

Alternatively, the benzothiazolones (I) of the invention are obtainable by reacting a compound of the formula:

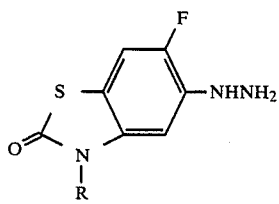

wherein R is as defined above with a compound of the formula:

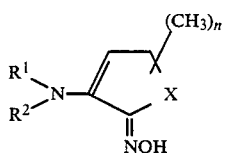

wherein X and n are each as defined above and $R^1$ and $R^2$ are, the same or different, each a $C_1$–$C_6$ alkyl group or, when taken together with the adjacent nitrogen atom, they represent a 5 to 7-membered nitrogen-containing heterocyclic ring optionally containing an oxygen atom, followed by oxidative ring closure.

The reaction between the compound (IV) and the compound (V) is normally accomplished in the presence of a small amount of an acid (e.g. acetic acid, p-toluenesulfonic acid) in a solvent such as alcohols (e.g. methanol, ethanol, cellosolve) or ethers (e.g. dioxane, tetrahydrofuran). In the reaction, the compound (V) may be used in 1 to 1.05 equivalents to the compound (IV). The oxidative ring closure is carried out in the existence of an oxidizing agent (e.g. cupric sulfate, platinum oxide, zinc tetraacetate) in a tertiary amine (e.g. pyridine, picoline) and a solvent such as water, alcohols (e.g. methanol, ethanol) or ethers (e.g. diethyl ether, diisopropyl ether, diethylene glycol dimethyl ether, dioxane, tetrahydrofuran) at a temperture of 10° to 100° C. for a period of 1 to 10 hours. The amount of the oxidizing agent and the tertiary amine are respectively from 1.0 to 1.5 equivalents and from 1 equivalent to a large excess to the compound (IV).

After completion of the reaction, the reaction mixture may be subjected to a post-treatment by a per se conventional procedure, for instance, dilution with water, extraction with an organic solvent and concentration. If necessary, any purification procedure such as chromatography or recrystallization may be adopted.

Typical examples of the benzothiazolones (I) which can be produced by any of the above procedures are shown in Table 1.

TABLE 1

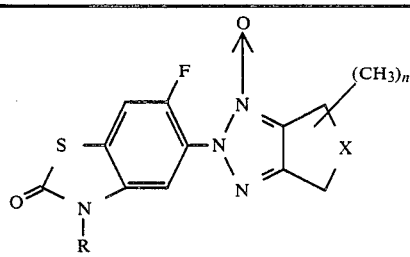

| R | X | n |
|---|---|---|
| $CH_3$ | $-CH_2-$ | 0 |
| $C_2H_5$ | $-CH_2-$ | 0 |
| $n-C_3H_7$ | $-CH_2-$ | 0 |
| $i-C_3H_7$ | $-CH_2-$ | 0 |
| $n-C_4H_9$ | $-CH_2-$ | 0 |
| $i-C_4H_9$ | $-CH_2-$ | 0 |
| $sec-C_4H_9$ | $-CH_2-$ | 0 |
| $CH_3$ | $-CH(CH_3)-$ | 0 |
| $C_2H_5$ | $-CH(CH_3)-$ | 0 |
| $n-C_3H_7$ | $-CH(CH_3)-$ | 0 |
| $i-C_3H_7$ | $-CH(CH_3)-$ | 0 |
| $sec-C_4H_9$ | $-CH(CH_3)-$ | 0 |
| $i-C_4H_9$ | $-CH(CH_3)-$ | 0 |
| $i-C_3H_7$ | $-C(CH_3)_2-$ | 0 |
| $i-C_3H_7$ | $-CH_2-$ | 1 |
| $i-C_3H_7$ | $-CH(CH_3)-$ | 1 |
| $i-C_3H_7$ | $-CH(CH_3)-$ | 2 |
| $i-C_3H_7$ | $-C(CH_3)_2-$ | 1 |
| $-CH_2CH=CH_2$ | $-CH_2-$ | 0 |
| $-CH_2CH=CH_2$ | $-CH(CH_3)-$ | 0 |
| $-CH_2CH=CH_2$ | $-C(CH_3)_2-$ | 0 |
| $-\underset{\underset{CH_3}{\vert}}{CH}CH=CH_2$ | $-CH_2-$ | 0 |
| $-\underset{\underset{CH_3}{\vert}}{CH}CH=CH_2$ | $-CH(CH_3)-$ | 0 |
| $-\underset{\underset{CH_3}{\vert}}{CH}CH=CH_2$ | $-C(CH_3)_2-$ | 0 |
| $-\underset{\underset{CH_3}{\vert}}{CH}CH=CH_2$ | $-CH_2-$ | 1 |
| $-\underset{\underset{CH_3}{\vert}}{CH}CH=CH_2$ | $-CH(CH_3)-$ | 1 |
| $-\underset{\underset{CH_3}{\vert}}{CH}CH=CH_2$ | $-C(CH_3)_2-$ | 1 |
| $-CH_2\underset{\underset{CH_3}{\vert}}{C}=CH_2$ | $-CH_2-$ | 0 |
| $-CH_2\underset{\underset{CH_3}{\vert}}{C}=CH_2$ | $-CH(CH_3)-$ | 0 |
| $-CH_2\underset{\underset{CH_3}{\vert}}{C}=CH_2$ | $-C(CH_3)_2-$ | 0 |
| $-CH_2CH{=}CHCH_3$ | $-CH_2-$ | 0 |
| $-CH_2CH{=}CHCH_3$ | $-CH(CH_3)-$ | 0 |

TABLE 1-continued

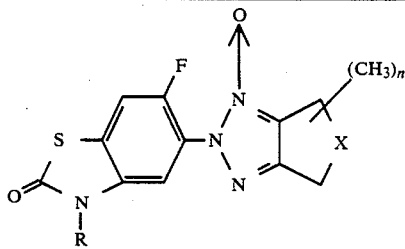

(I)

| R | X | n |
|---|---|---|
| —CH₂CH=CHCH₃ | —C(CH₃)₂— | 0 |
| —CHCH=C(CH₃)₂ | —CH₂— | 0 |
| —CHC=CH(CH₃)<br>\|<br>CH₃ | —CH₂— | 0 |
| —CH₂C≡CH | —CH₂— | 0 |
| —CH₂C≡CH | —CH(CH₃)— | 0 |
| —CH₂C≡CH | —C(CH₃)₂— | 0 |
| —CH₂C≡CH | —CH₂— | 1 |
| —CH₂C≡CH | —CH(CH₃)— | 1 |
| —CH₂C≡CH | —C(CH₃)₂— | 1 |
| —CH₂C≡CH | —CH₂— | 2 |
| —CH₂C≡CH | —CH(CH₃)— | 2 |
| —CHC≡CH<br>\|<br>CH₃ | —CH₂— | 0 |
| —CHC≡CH<br>\|<br>CH₃ | —CH(CH₃)— | 0 |
| —CHC≡CH<br>\|<br>CH₃ | —C(CH₃)₂— | 0 |
| —CHC≡CH<br>\|<br>CH₃ | —CH₂— | 1 |
| —CHC≡CH<br>\|<br>CH₃ | —CH(CH₃)— | 1 |
| —CH₂C≡CCH₃ | —CH₂— | 0 |
| —CH₂C≡CCH₃ | —CH(CH₃)— | 0 |
| —CH₂C≡CCH₃ | —C(CH₃)₂— | 0 |
| CH₃ | —(CH₂)₂— | 0 |
| C₂H₅ | —(CH₂)₂— | 0 |
| n-C₃H₇ | —(CH₂)₂— | 0 |
| i-C₃H₇ | —(CH₂)₂— | 0 |
| n-C₄H₉ | —(CH₂)₂— | 0 |
| i-C₄H₉ | —(CH₂)₂— | 0 |
| sec-C₄H₉ | —(CH₂)₂— | 0 |
| n-C₅H₁₁ | —(CH₂)₂— | 0 |
| i-C₅H₁₁ | —(CH₂)₂— | 0 |
| sec-C₅H₁₁ | —(CH₂)₂— | 0 |
| neo-C₅H₁₁ | —(CH₂)₂— | 0 |
| n-C₆H₁₃ | —(CH₂)₂— | 0 |
| i-C₆H₁₃ | —(CH₂)₂— | 0 |
| sec-C₆H₁₃ | —(CH₂)₂— | 0 |
| —CH₂CH(C₂H₅)₂ | —(CH₂)₂— | 0 |
|     CH₃<br>\|<br>—CHCHCH₂CH₃<br>\|<br>CH₃ | —(CH₂)₂— | 0 |
| CH₃ | —CH(CH₃)CH₂— | 0 |

TABLE 1-continued

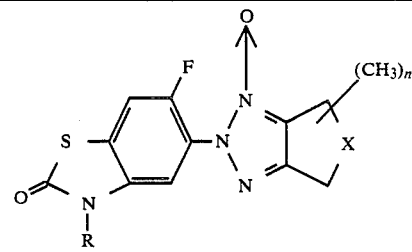

(I)

| R | X | n |
|---|---|---|
| C₂H₅ | —CH(CH₃)CH₂— | 0 |
| n-C₃H₇ | —CH(CH₃)CH₂— | 0 |
| i-C₃H₇ | —CH(CH₃)CH₂— | 0 |
| n-C₄H₉ | —CH(CH₃)CH₂— | 0 |
| i-C₄H₉ | —CH(CH₃)CH₂— | 0 |
| sec-C₄H₉ | —CH(CH₃)CH₂— | 0 |
| n-C₅H₁₁ | —CH(CH₃)CH₂— | 0 |
| i-C₅H₁₁ | —CH(CH₃)CH₂— | 0 |
| sec-C₅H₁₁ | —CH(CH₃)CH₂— | 0 |
| neo-C₅H₁₁ | —CH(CH₃)CH₂— | 0 |
| CH₃ | —C(CH₃)₂CH₂— | 0 |
| C₂H₅ | —C(CH₃)₂CH₂— | 0 |
| n-C₃H₇ | —C(CH₃)₂CH₂— | 0 |
| i-C₃H₇ | —C(CH₃)₂CH₂— | 0 |
| sec-C₄H₉ | —C(CH₃)₂CH₂— | 0 |
| C₂H₅ | —CH(CH₃)CH(CH₃)— | 0 |
| n-C₃H₇ | —CH(CH₃)CH(CH₃)— | 0 |
| i-C₃H₇ | —CH(CH₃)CH(CH₃)— | 0 |
| sec-C₄H₁₁ | —CH(CH₃)CH(CH₃)— | 0 |
| CH₃ | —(CH₂)₂— | 1 |
| C₂H₅ | —(CH₂)₂— | 1 |
| n-C₃H₇ | —(CH₂)₂— | 1 |
| i-C₃H₇ | —(CH₂)₂— | 1 |
| n-C₄H₉ | —(CH₂)₂— | 1 |
| i-C₄H₉ | —(CH₂)₂— | 1 |
| sec-C₄H₉ | —(CH₂)₂— | 1 |
| C₂H₅ | —CH₂CH(CH₃)— | 1 |
| n-C₃H₇ | —CH₂CH(CH₃)— | 1 |
| i-C₃H₇ | —CH₂CH(CH₃)— | 1 |
| sec-C₃H₇ | —CH₂CH(CH₃)— | 1 |
| i-C₃H₇ | —CH₂C(CH₃)₂— | 1 |
| i-C₃H₇ | —CH(CH₃)CH(CH₃)— | 1 |
| C₂H₅ | —OCH₂— | 0 |
| n-C₃H₇ | —OCH₂— | 0 |
| i-C₃H₇ | —OCH₂— | 0 |
| n-C₄H₉ | —OCH₂— | 0 |
| i-C₄H₉ | —OCH₂— | 0 |
| sec-C₄H₉ | —OCH₂— | 0 |
| —CH₂CH=CH₂ | —(CH₂)₂— | 0 |
| —CH₂CH=CH₂ | —CH(CH₃)CH₂— | 0 |
| —CH₂CH=CH₂ | —CH(CH₃)CH(CH₃)— | 0 |
| —CH₂CH=CH₂ | —C(CH₃)₂CH₂— | 0 |
| —CH₂CH=CH₂ | —(CH₂)₂— | 1 |
| —CH₂CH=CH₂ | —CH(CH₃)CH₂— | 1 |
| —CH₂CH=CH₂ | —CH(CH₃)CH(CH₃)— | 1 |
| —CHCH=CH₂<br>\|<br>CH₃ | —(CH₂)₂— | 0 |
| —CHCH=CH₂<br>\|<br>CH₃ | —CH(CH₃)CH₂— | 0 |
| —CHCH=CH₂<br>\|<br>CH₃ | —CH(CH₃)CH(CH₃)— | 0 |
| —CHCH=CH₂<br>\|<br>CH₃ | —CH₂C(CH₃)₂— | 0 |
| —CHCH=CH₂<br>\|<br>CH₃ | —(CH₂)₂— | 1 |

TABLE 1-continued

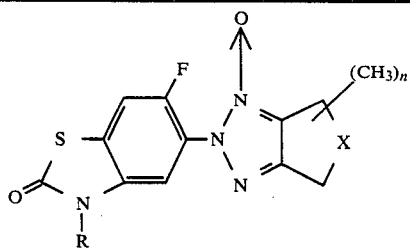

(I)

| R | X | n |
|---|---|---|
| —CH₂C(CH₃)=CH₂ | —(CH₂)₂— | 0 |
| —CH₂C(CH₃)=CH₂ | —CH(CH₃)CH₂— | 0 |
| —CH₂C(CH₃)=CH₂ | —C(CH₃)₂CH₂— | 0 |
| —CH₂C(CH₃)=CH₂ | —(CH₂)₂— | 1 |
| —CH₂CH=CHCH₃ | —(CH₂)₂— | 0 |
| —CH₂CH=CHCH₃ | —CH(CH₃)CH₂— | 0 |
| —CH₂CH=CHCH₃ | —(CH₂)₂— | 1 |
| —CH₂C≡CH | —(CH₂)₂— | 0 |
| —CH₂C≡CH | —CH(CH₃)CH₂— | 0 |
| —CH₂C≡CH | —CH(CH₃)CH(CH₃)— | 0 |
| —CH₂C≡CH | —CH₂C(CH₃)₂— | 0 |
| —CH₂C≡CH | —(CH₂)₂— | 1 |
| —CH₂C≡CH | —(CH₂)₂— | 2 |
| —CH₂C≡CH | —CH(CH₃)CH(CH₂)— | 1 |
| —CH₂C≡CH | —CH(CH₃)CH₂— | 1 |
| —CH₂C≡CH | —CH₂C(CH₃)₂— | 1 |
| —CHC≡CH, CH₃ | —(CH₂)₂— | 0 |
| —CHC≡CH, CH₃ | —CH(CH₃)CH₂— | 0 |
| —CHC≡CH, CH₃ | —CH(CH₃)CH(CH₃)— | 0 |
| —CHC≡CH, CH₃ | —CH₂C(CH₃)₂— | 0 |
| —CHC≡CH, CH₃ | —(CH₂)₂— | 1 |
| —CHC≡CH, CH₃ | —CH(CH₃)CH₂— | 1 |
| —CH₂C≡CCH₃ | —(CH₂)₂— | 0 |
| —CH₂C≡CCH₃ | —CH₂CH(CH₃)— | 0 |
| —CH₂C≡CCH₃ | —CH(CH₃)CH(CH₃)— | 0 |
| —CH₂C≡CCH₃ | —(CH₂)₂— | 1 |
| —CH₂CH=CH₂ | —OCH₂— | 0 |
| —CHCH=CH₂, CH₃ | —OCH₂— | 0 |

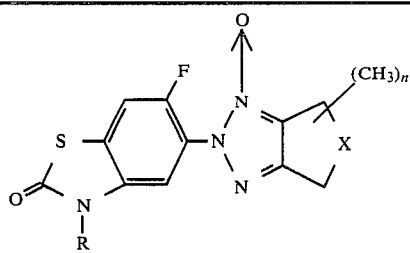

(I)

| R | X | n |
|---|---|---|
| —CH₂C(CH₃)=CH₂ | —OCH₂— | 0 |
| —CH₂CH=CH, CH₃ | —OCH₂— | 0 |
| —CH₂C≡CH | —OCH₂— | 0 |
| —CHC≡CH, CH₃ | —OCH₂— | 0 |
| —CH₂C≡CCH₃ | —OCH₂— | 0 |
| —CH₂OCH₃ | —CH₂— | 0 |
| —CH₂OC₂H₅ | —CH₂— | 0 |
| —CH₂O(n)C₃H₇ | —CH₂— | 0 |
| —CH₂O(n)C₄H₉ | —CH₂— | 0 |
| —CH₂OCH₃ | —(CH₂)₂— | 0 |
| —CH₂OC₂H₅ | —(CH₂)₂— | 0 |
| —CH₂O(n)C₃H₇ | —(CH₂)₂— | 0 |
| —CH₂O(n)C₄H₉ | —(CH₂)₂— | 0 |
| —CH₂CH₂OCH₃ | —(CH₂)₂— | 0 |
| —CH₂CH₂OC₂H₅ | —(CH₂)₂— | 0 |
| —CH₂OCH₃ | —OCH₂— | 0 |
| —CH₂OC₂H₅ | —OCH₂— | 0 |
| —CH₂OCH₃ | —CH₂CH(CH₃)— | 0 |
| —CH₂OCH₃ | —CH(CH₃)CH(CH₃)— | 0 |
| i-C₃H₇ | —(CH₂)₃— | 0 |
| —CH₂CH=CH₂ | —(CH₂)₃— | 0 |
| —CH₂C≡CH | —(CH₂)₃— | 0 |
| CF₃ | —CH(CH₃)CH₂— | 0 |
| CF₃ | —CH(CH₃)CH(CH₃)— | 0 |
| —CF₂H | —CH₂— | 0 |
| —CF₂H | —CH(CH₃)— | 0 |
| —CF₂H | —C(CH₃)₂— | 0 |
| —CF₂H | —(CH₂)₂— | 0 |
| —CF₂H | —CH(CH₃)CH₂— | 0 |
| —CF₂H | —CH(CH₃)CH(CH₃)— | 0 |
| —CF₂CF₂CH₃ | —(CH₂)— | 0 |
| —CF₂CF₂CH₃ | —CH(CH₃)— | 0 |
| —CF₂CF₂CH₃ | —C(CH₃)₂— | 0 |
| —CF₂CF₂CH₃ | —(CH₂)₂— | 0 |
| —CF₂CF₂CH₃ | —CH(CH₃)CH₂— | 0 |
| —CF₂CF₂CH₃ | —CH(CH₃)CH(CH₃)— | 0 |
| —CH₂SCH₃ | —CH₂— | 0 |
| —CH₂SCH₃ | —CH(CH₃)— | 0 |
| —CH₂SCH₃ | —C(CH₃)₂— | 0 |
| —CH₂SCH₃ | —(CH₂)₂— | 0 |
| —CH₂SCH₃ | —CH(CH₃)CH₂— | 0 |
| —CH₂SCH₃ | —CH(CH₃)CH(CH₃)— | 0 |
| —CH₂SC₂H₅ | —CH₂— | 0 |
| —CH₂SC₂H₅ | —CH(CH₃)— | 0 |
| —CH₂SC₂H₅ | —C(CH₃)₂— | 0 |
| —CH₂SC₂H₅ | —(CH₂)₂— | 0 |
| —CH₂SC₂H₅ | —CH(CH₃)CH₂— | 0 |
| —CH₂SC₂H₅ | —CH(CH₃)CH(CH₃)— | 0 |
| —CH(CH₃)SCH₃ | —CH₂— | 0 |
| —CH(CH₃)SCH₃ | —CH(CH₃)— | 0 |
| —CH(CH₃)SCH₃ | —C(CH₃)₂— | 0 |
| —CH(CH₃)SCH₃ | —(CH₂)₂— | 0 |
| —CH(CH₃)SCH₃ | —CH(CH₃)CH₂— | 0 |
| —CH(CH₃)SCH₃ | —CH(CH₃)CH(CH₃)— | 0 |
| —CH(CH₃)SC₂H₅ | —CH₂— | 0 |
| —CH(CH₃)SC₂H₅ | —CH(CH₃)— | 0 |
| —CH(CH₃)SC₂H₅ | —C(CH₃)₂— | 0 |

TABLE 1-continued (I) [Structure shown: benzothiazolone with F, S, C(=O)N(R), connected to N-triazole ring with (CH3)n and X, with N-oxide]

| R | X | n |
|---|---|---|
| —CH(CH₃)SC₂H₅ | —(CH₂)₂— | 0 |
| —CH(CH₃)SC₂H₅ | —CH(CH₃)CH₂— | 0 |
| —CH(CH₃)SC₂H₅ | —CH(CH₃)CH(CH₃)— | 0 |

Some typical embodiments of the invention for production of the benzothiazolones (I) are illustratively shown in the following Examples.

EXAMPLE 1

To a dispersion of sodium hydride (60% oil; 31 mg) in dry N,N-dimethylformamide (3 ml) was added 2-[6fluoro-2(3H)-benzothiazolon-5-yl]-4,5,6,7-tetrahydro-2H-benzotriazole-1-oxide (220 mg) at 0° C., and the resultant mixture was stirred at the same temperature for 30 minutes, followed by addition of propargyl bromide (94 mg). The mixture was allowed to react at 50° to 60° C. for 3 hours. Water was added to the reaction mixture, which was then extracted with ethyl acetate. The extract was washed with water, dried and concentrated. The residue was purified by silica gel thin layer chromatography using a mixture of ethyl acetate and toluene (1:9) as an eluent to give 2-[3-(2-propynyl)-6-fluoro-2(3H)-benzothiazolon-5-yl]-4,5,6,7-tetrahydro-2H-benzotriazole-1-oxide (Compound No. 5; 120 mg). $n^{25.4}_D$ 1.5988.

EXAMPLE 2

6-Fluoro-3-(1-methylethyl)-2(3H)-benzothiazolon5-ylhydrazine (1.11 g) and 4-(3-hydroxyimino1-cyclohexen2-yl)morpholine (0.90 g) were dissolved in ethanol (20 ml), a catalytic amount of acetic acid was added thereto, and the resultant mixture was heated under reflux for 3 hours. Water was added to the reaction mixture, which was then extracted with ethyl acetate. The extract was distilled under reduced pressure to remove the solvent and combined with a mixture of 15% aqueous pyridine (30 ml), tetrahydrofuran (20 ml) and cupric sulfate pentahydrate (2.2 g), followed by refluxing for 2 hours. After cooling, water and ethyl acetate were added to the reaction mixture. The organic layer was separated from the water layer, washed with dilute hydrochloric acid, dried and concentrated. The residue was crystallized from ether to give 2-[3-isopropyl6-fluoro-2(3H)-benzothiazolon-5-yl]-4,5,6,7-tetrahydro-2H-benzotriazole-1-oxide (Compound No. 3; 0.7 g). m.p., 92.5° C.

In the same manner as above, the benzothiazolones (I) as shown in Table 2 were prepared.

TABLE 2

(I) [Structure shown]

| Compound No. | R | [triazole ring structure] | Physical property |
|---|---|---|---|
| 1 | C₂H₅ | [tetrahydrobenzotriazole-1-oxide] | $n_D^{24.5}$ 1.5940 |
| 2 | n-C₃H₇ | [tetrahydrobenzotriazole-1-oxide] | m.p., 141–142° C. |
| 3 | i-C₃H₇ | [tetrahydrobenzotriazole-1-oxide] | m.p., 92.5° C. |

TABLE 2-continued
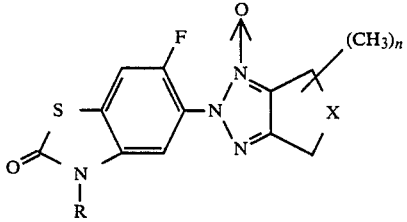
(I)
| Compound No. | R | 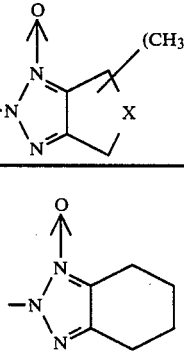 | Physical property |
|---|---|---|---|
| 4 | —CH$_2$CH=CH$_2$ | 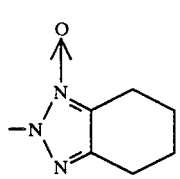 | $n_D^{24.5}$ 1.5964 |
| 5 | —CH$_2$C≡CH | 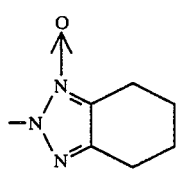 | $n_D^{25.4}$ 1.5988 |
| 6 | —CH$_2$OCH$_3$ | 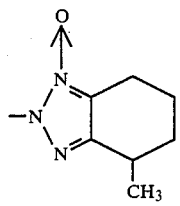 | m.p., 139–140° C. |
| 7 | i-C$_3$H$_7$ | 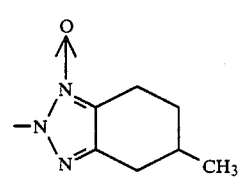 | glassy |
| 8 | i-C$_3$H$_7$ | 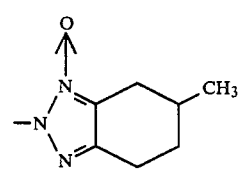 | glassy |
| 9 | i-C$_3$H$_7$ | 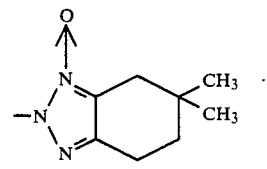 | glassy |
| 10 | i-C$_3$H$_7$ | | glassy |

TABLE 2-continued
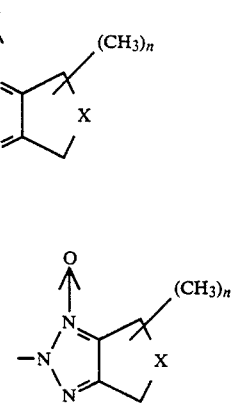
(I)
| Compound No. | R | | Physical property |
|---|---|---|---|
| 11 | i-C₃H₇ | 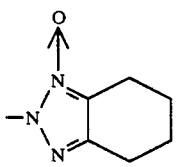 | m.p., 145–146° C. |
| 12 | i-C₃H₇ | 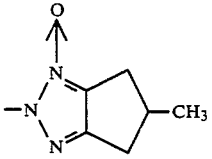 | glassy |
| 13 | i-C₃H₇ | 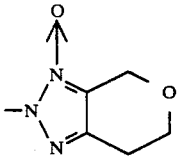 | m.p., 185.7° C. |
| 14 | —CH₂CH₂F | 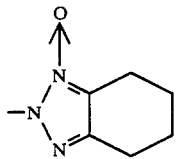 | resinous |
| 15 | —CH(CH₃)OCH₃ | 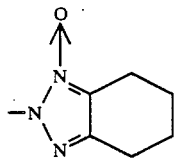 | m.p., 175–175.5° C. |
| 16 | —CH(CH₃)OC₂H₅ | 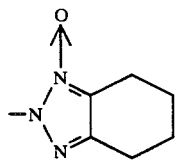 | m.p., 168.5–169° C. |
| 17 | —CH₂SCH₃ | 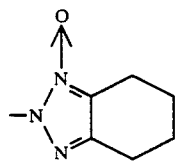 | m.p., 179–180° C. |

The starting compounds (II) and (IV) in the process of this invention may be produced according to the following scheme:

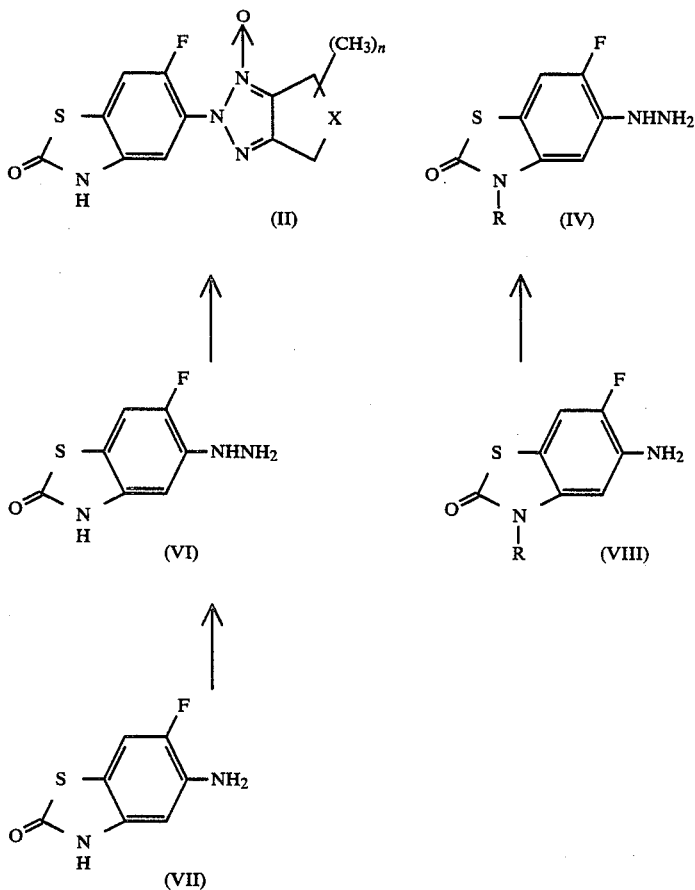

where R, X and n are each as defined above.

Each reaction as set forth above will be hereinafter explained in detail.

(1) Production of the compound (II) from the compound (VI):

In the same manner as in the conversion of the compound (IV) to the benzothiazolone (I), 6-fluoro-2(3H)-benzothiazolon-5-ylhydrazine (VI) is reacted with 1 to 1.05 equivalents of the compound (V) in a solvent such as alcohols (e.g. methanol, ethanol, cellosolve) or ethers (e.g. 1,4-dioxane, tetrahydrofuran) in the presence of a small amount of an acid (e.g. acetic acid, p-toluenesulfonic acid) and then reacting the resultant product with 1 to 1.5 equivalents of an oxidizing agent (e.g. cupric sulfate, platinum oxide, zinc tetraacetate) in 1 equivalent to large excess of a tertiary amine (e.g. pyridine) and a solvent such as water, alcohols (e.g. methanol, ethanol) or ethers (e.g. 1,4-dioxane, tetrahydrofuran, diethyl ether, diisopropyl ether, diethylene glycol dimethyl ether) at a temperature of 10° to 100° C. for a period of 1 to 10 hours.

After completion of the reaction, the reaction mixture may be post-treated by a per se conventional procedure such as dilution with water, extraction with an organic solvent and concentration. If desired, the reaction product may be further purified by means of chromatography or recrystallization.

A typical example for production of the compound (II) is illustratively shown in the following Example.

EXAMPLE 3

6-Fluoro-2(3H)-benzothiazolon-5-ylhydrazine (6.60 g) and 4-(2-hydroxyimino-1(6)-cyclohexen-1-yl)morpholine (6.50 g) were dissolved in ethanol (120 ml), a catalytic amount of acetic acid was added thereto, and the resulting mixture was heated under reflux for 5 hours. Water was added thereto, and the reaction mixture was extracted with ethyl acetate. The extract was concentrated, a mixture of cupric sulfate pentahydrate (16.0 g), water (64 g), 15% aqueous pyridine (160 g) and tetrahydrofuran (128 ml) was added thereto, and the resulting mixture was refluxed for 5 hours. After cooling, water and ethyl acetate were added thereto. The organic layer was separated from the aqueous layer, washed with dilute hydrochloric acid, dried and concentrated. The residue was purified by silica gel column chromatography using a mixture of ethyl acetate and hexane (1:9) as an eluent to give 2-[6-fluoro-2(3H)-benzothiazolon-5-yl]-4,5,6,7-tetrahydro-2H-benzotriazole-1-oxide (0.62 g).

$^1$H-NMR ($\delta$, CDCl$_3$+DMSO-d$_6$): 1.5–2.2 (br, 4H), 2.3–2.9 (br, 4H), 7.21 (d, 1H, J=6 Hz), 7.46 (d, 1H, J=9 Hz).

(2) Production of the compound (VI) from the compound (VII) and production of the compound (IV) from the compound (VIII):

The compounds (IV) and (VI) are obtainable according to the method as described in J.Chem.Soc., (c), 1970, 2106. Namely, the compound (IV) or (VI) may be prepared by treating the compound (VIII) or (VII) with an alkali metal nitrite (e.g. sodium nitrite, potassium nitrite) in the presence of a mineral acid (e.g. sulfuric acid, hydrochloric acid) at a temperature of about −5° to 5° C. for a period of about 0.5 to 24 hours, followed by treatment of the resultant diazo compound with a reducing agent (e.g. stannous chloride, zinc, sodium sulfite) at a temperature of about −20° to 50° C. for a period of about 1 to 24 hours. In the reaction, each of the alkali metal nitrite and the reducing agent may be used in an amount of about 1 to 2 equivalents to the compound (VIII) or (VII).

When crystals were precipitated in the reaction mixture, they are collected by filtration, dissolved in water, neutralized with an alkali and extracted with an organic solvent. When not precipitated, the reaction mixture is neutralized with an alkali and extracted with an organic solvent. The extract is washed with water, dried and concentrated, if necessary, followed by purification such as chromatography.

A typical example for production of the compound (IV) or the compound (VI) is illustratively shown in the following Example.

EXAMPLE 4

A suspension of 5-amino-6-fluoro-2(3H)-benzothiazolone (12.98 g) in conc. hydrochloric acid (70 g) was cooled to 0° to 5° C., and a saturated aqueous solution of sodium nitrite (5.08 g) was dropwise added thereto at 0° to 5° C., followed by stirring at the same temperature for 30 minutes. The resultant mixture was cooled to −20° C., and a solution of stannous chloride (28.06 g) in conc. hydrochloric acid (30 g) was added thereto all at once, followed by stirring at 0° C. for 2 hours. The reaction mixture was neutralized with potassium hydroxide, a colloidal substance originated from stannous chloride was removed by celite and the resultant solution was extracted with ethyl acetate. The extract was washed with water, dried over magnesium sulfate and concentrated to give 6-fluoro-2(3H)-benzothiazolon-5-ylhydrazine (6.60 g).

$^1$H-NMR ($\delta$, CDCl$_3$+DMSO-d$_6$) 3.5–4.5 (br, 2H), 5.7–6.3 (br, 1H), 6.97 (d, 1H, J=9 Hz), 7.00 (d, 1H, J=6 Hz).

In the same manner as above, the compounds (IV) and (VI) as shown in Table 3 were obtained.

TABLE 3

(IV or VI)

[Structure: benzothiazolone with F and NHNH$_2$ substituents, with N-R group]

| R | Physical property |
|---|---|
| H | $^1$H-NMR ($\delta$, CDCl$_3$ + DMSO-d$_6$): 3.5–4.5 (br, 2H), 5.7–6.3 (br, 1H), 6.97 (d, 1H, J = 9Hz), 7.00 (d, 1H, J = 6Hz) |
| i-C$_3$H$_7$ | m.p., 66° C. |
| —CH$_2$CH=CH$_2$ | m.p., 129.7° C. |
| —CH$_2$C≡CH | m.p., 181.8° C. |

For the practical use of the benzothiazolones (I), they are usually formulated with conventional solid or liquid carriers or diluents as well as surface active agents or auxiliary agents into conventional preparation forms such as emulsifiable concentrates, wettable powders, suspensions and granules. The content of the benzothiazolone (I) as the active ingredient in such preparation forms is usually within a range of about 0.05 to 90% by weight, preferably of about 0.1 to 80% by weight. Examples of the solid carrier or diluent are fine powders or granules of kaolin clay, attapulgite clay, bentonite, terra alba, pyrophyllite, talc, diatomaceous earth, calcite, walnut powders, urea, ammonium sulfate and synthetic hydrous silicate, etc. As the liquid carrier or diluent, there may be exemplified aromatic hydrocarbons (e.g. xylene, methylnaphthalene), alcohols (e.g. isopropanol, ethylene glycol, cellosolve), ketones (e.g. acetone, cyclohexanone, isophorone), soybean oil, cotton seed oil, dimethylsulfoxide, N,N-dimethylformamide, acetonitrile, water, etc.

The surface active agent used for emulsification, dispersion or spreading may be of any type, for instance, either anionic or non-ionic. Examples of the surface active agent include alkylsulfates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene polyoxypropylene block copolymer, sorbitan fatty acid esters, polyoxyethylene sorbitan fatty acid esters, etc. Examples of the auxiliary agents include ligninsulfonates, sodium alginate, polyvinyl alcohol, gum arabic, CMC (carboxymethyl cellulose), PAP (isopropyl acid phosphate), etc.

Practical embodiments of the herbicidal composition according to the present invention are illustratively shown in the following examples wherein parts are by weight. The compound number of the active ingredient corresponds to the one in Table 2.

FORMULATION EXAMPLE 1

Fifty parts of Compound No. 2 or 11, 3 parts of calcium ligninsulfonate, 2 parts of sodium laurylsulfate and 45 parts of synthetic hydrous silicate are mixed well while being powdered to obtain a wettable powder.

FORMULATION EXAMPLE 2

Ten parts of Compound No. 3 or 4, 14 parts of polyoxyethylenestyrylphenyl ether, 6 parts of calcium dodecylbenzenesulfonate, 25 parts of xylene and 45 parts of cyclohexanone are mixed well to obtain an emulsifiable concentrate.

FORMULATION EXAMPLE 3

Two parts of Compound No. 6 or 8, 1 part of synthetic hydrous silicate, 2 parts of calcium ligninsulfonate, 30 parts of bentonite and 65 parts of kaolin clay are mixed well while being powdered. The mixture is then kneaded with water, granulated and dried to obtain granules.

FORMULATION EXAMPLE 4

Twenty-five parts of Compound No. 7 or 9 is mixed with 3 parts of polyoxyethylene sorbitan monooleate, 3 parts of carboxymethyl cellulose and 69 parts of water and pulverized until the particle size of the mixture becomes less than 5 microns to obtain a suspension.

FORMULATION EXAMPLE 5

Five parts of Compound No. 5, 9 or 13, 14 parts of polyoxyethylenestyrylphenyl ether, 6 parts of calcium dodecylbenzenesulfonate, 30 parts of xylene and 45 parts of N,N-dimethylformamide are mixed well to obtain an emulsifiable concentrate.

The benzothiazolones (I) thus formulated in any suitable preparation form are useful for pre-emergence or post-emergence control of undesired weeds by soil or foliar treatment as well as flood fallowing treatment. These treatments include the application to the soil surface prior to or after the transplanting or the incorporation into the soil. The foliar treatment may be effected by spraying the herbicidal composition containing the benzothiazolones (I) over the top of the plants. It may also be applied directly to the weeds if care is taken to keep the chemical off the crop foliage.

The benzothiazolones (I) of the present invention may be used together with other herbicides to improve their activity as herbicides, and in some cases, a synergistic effect can be expected. Further, they may be applied in combination with insecticides, acaricides, nematocides, fungicides, plant growth regulators, fertilizers, soil improvers, etc.

Furthermore, the benzothiazolones (I) can be used as herbicides applicable to agricultural plowed fields as well as paddy fields. They are also useful as herbicides to be employed for orchards, pasture land, lawns, forests, nonagricultural fields, etc.

The dosage rate of the benzothiazolones (I) may vary depending on the prevailing weather conditions, the formulation used, the prevailing season, the mode of application, the soil involved, the crop and weed species, etc. Generally, however, the dosage rate is from 0.02 to 100 grams, preferably from 0.05 to 50 grams, of the active ingredient per are. The herbicidal composition of the invention formulated in the form of an emulsifiable concentrate, a wettable powder or a suspension may ordinarily be employed by diluting it with water at a volume of about 1 to 10 liters per are, if necessary, with addition of an auxiliary agent such as a spreading agent. Examples of the spreading agent include, in addition to the surface active agents as noted above, polyoxyethylene resin acid (ester), ligninsulfonate, abietylenic acid salt, dinaphthylmethanedisulfonate, paraffin, etc. The composition formulated in the form of granules may be normally applied as such without dilution.

The biological data of the benzothiazolones (I) as herbicides will be illustratively shown in the following Examples wherein the phytotoxicity to crop plants and the herbicidal activity on weeds were observed visually as to the degree of germination as well as the growth inhibition and rated with an index 0, 1, 2, 3, 4, 5, 6, 7, 8, 9 or 10, in which the numeral "0" indicates no material difference as seen in comparison with the untreated plant and the numeral "10" indicates the complete inhibition or death of the test plants.

The following compound was used for comparison.

| Compound No. | Chemical structure | Remarks |
|---|---|---|
| A | Cl, CH$_2$COOH, N, =O, S (benzothiazole structure) | Commercially available herbicide "benazolin" |

TEST EXAMPLE 1

Cylindrical plastic pots (diameter, 10 cm; height, 10 cm) were filled with upland field soil, and the seeds of Japanese millet, tall morningglory and velvetleaf were sowed therein and covered with soil. A designated amount of the test compound formulated in an emulsifiable concentrate as in Formulation Example 2 was diluted with water, and the dilution was sprayed onto the soil surface by means of a small hand sprayer at a spray volume of 10 liters per are. The test plants were further grown in a greenhouse for 20 days, and the herbicidal activity was examined. The results are shown in Table 4.

TABLE 4

| Compound No. | Dosage (g/are) | Herbicidal activity | | |
|---|---|---|---|---|
| | | Japanese millet | Tall morning-glory | Velvet-leaf |
| 1 | 20 | 10 | 10 | 10 |
| 2 | 20 | 10 | 10 | 10 |
| 3 | 20 | 10 | 10 | 10 |
| 4 | 20 | 10 | 10 | 10 |
| 5 | 20 | 10 | 10 | 10 |
| 6 | 20 | 10 | 10 | 10 |
| 7 | 20 | 10 | 10 | 10 |
| 8 | 20 | 10 | 10 | 10 |
| 9 | 20 | 10 | 10 | 10 |
| 10 | 20 | 10 | 10 | 10 |
| 11 | 20 | 10 | 10 | 10 |
| 12 | 20 | 10 | 10 | 10 |
| 13 | 20 | 10 | 10 | 10 |
| 14 | 20 | 10 | 10 | 10 |
| 15 | 20 | 10 | 10 | 10 |
| 16 | 20 | 10 | 10 | 10 |
| 17 | 20 | 10 | 10 | 10 |

TEST EXAMPLE 2

Cylindrical plastic pots (diameter, 10 cm; height, 10 cm) were filled with upland field soil, and the seeds of Japanese millet, radish and velvetleaf were sowed therein and cultivated in a greenhouse for 10 days. A designated amount of the test compound formulated in an emulsifiable concentrate as in Formulation Example 2 was diluted with water containing a spreading agent, and the dilution was sprayed over the foliage of the test plants by means of a small hand sprayer at a spray volume of 10 liters per are. The test plants were further grown in the greenhouse for 20 days, and the herbicidal activity was examined. The results are shown in Table 5.

TABLE 5

| Compound No. | Dosage (g/are) | Herbicidal activity | | |
|---|---|---|---|---|
| | | Japanese millet | Radish | Velvetleaf |
| 1 | 20 | 10 | 10 | 10 |
| 2 | 20 | 10 | 10 | 10 |
| 3 | 20 | 10 | 10 | 10 |
| 4 | 20 | 10 | 10 | 10 |
| 5 | 20 | 10 | 10 | 10 |
| 6 | 20 | 10 | 10 | 10 |
| 7 | 20 | 10 | 10 | 10 |
| 8 | 20 | 10 | 10 | 10 |
| 9 | 20 | 10 | 10 | 10 |
| 10 | 20 | 10 | 10 | 10 |
| 11 | 20 | 10 | 10 | 10 |
| 12 | 20 | 10 | 10 | 10 |
| 13 | 20 | 10 | 10 | 10 |
| 14 | 20 | 10 | 10 | 10 |
| 15 | 20 | 10 | 10 | 10 |
| 16 | 20 | 10 | 10 | 10 |
| 17 | 20 | 10 | 10 | 10 |

TEST EXAMPLE 3

Cylindrical plastic pots (diameter, 8 cm,; height, 12 cm) were filled with paddy field soil, and the seeds of barnyardgrass (*Echinochloa oryzicola*), broad-leaved weeds (i.e. common falsepimpernel, indian toothcup, waterwort) were sowed in 1 to 2 cm depth. Water was poured therein to make a flooded condition, and tubers of arrowhead were transplanted therein, and the test plants were grown in a greenhouse. Six days (at that time weeds began to germinate) thereafter, a designated amount of the test compound formulated in an emulsifiable concentrate as in Formulation Example 2 or 5 and diluted with water (5 ml) was applied to the pots by perfusion. The test plants were grown for an additional 20 days in the greenhouse, and the herbicidal activity was examined. The results are shown in Table 6.

TABLE 6

| Compound No. | Dosage (g/are) | Herbicidal activity | | |
|---|---|---|---|---|
| | | Barnyard-grass | Broad-leaved weed | Arrow-head |
| 3 | 0.63 | 9 | 10 | 10 |
| 4 | 0.63 | 9 | 10 | 10 |
| 5 | 0.63 | 10 | 10 | 10 |
| 8 | 0.63 | 10 | 10 | 10 |
| 9 | 0.63 | 10 | 10 | 10 |
| 11 | 0.63 | 10 | 10 | 10 |
| 13 | 0.63 | 9 | 10 | 10 |
| A | 0.63 | 0 | 1 | 0 |

TEST EXAMPLE 4

Vats (33 cm×23 cm×11 cm) were filled with upland field soil, and the seeds of cotton, common cocklebur, black nightshade, barnyardgrass (*Echinochloa crus-galli*) and johnsongrass were sowed therein to 1 to 2 cm depth. A designated amount of the test compound formulated in an emulsifiable concentrate as in Formulation Example 2 or 5 was diluted with water, and the dilution was sprayed onto the soil surface by means of a small hand sprayer at a spray volume of 10 liters per are. The test plants were further grown outdoors for 20 days, and the herbicidal activity was examined. The results are shown in Table 7.

TABLE 7

| Compound No. | Dosage (g/are) | Herbicidal activity | | | | |
|---|---|---|---|---|---|---|
| | | Cotton | Common cock-lebur | Black night-shade | Barn-yard-grass | Johnson-grass |
| 1 | 1.25 | 0 | 10 | 10 | 10 | 10 |
| 2 | 1.25 | 1 | 10 | 10 | 9 | 10 |
| 6 | 1.25 | 0 | 10 | 10 | 10 | 10 |
| A | 1.25 | 0 | 0 | 0 | 0 | 0 |

TEST EXAMPLE 4

Vats (33 cm×23 cm×11 cm) were filled with upland field soil, and the seeds of rice plant, velvetleaf, black nightshade, barnyardgrass (*Echinochloa crus-galli*) and green foxtail were sowed therein to 1 to 2 cm depth. A designated amount of the test compound formulated in an emulsifiable concentrate as in Formulation Example 2 or 5 was diluted with water, and the dilution was sprayed onto the soil surface by means of a small hand sprayer at a spray volume of 10 liters per are. The test plants were further grown in a greenhouse for 20 days, and the herbicidal activity was examined. The results are shown in Table 8.

TABLE 8

| Compound No. | Dosage (g/are) | Herbicidal activity | | | | |
|---|---|---|---|---|---|---|
| | | Rice plant | Velvet-leaf | Black night-shade | Barn-yard-grass | Green foxtail |
| 7 | 2.5 | 1 | 10 | 9 | — | 8 |
| 8 | 2.5 | 1 | 10 | 9 | 7 | 7 |
| 9 | 2.5 | 1 | 10 | 10 | 8 | 10 |
| 10 | 2.5 | 0 | 10 | — | — | 10 |
| A | 2.5 | 0 | 0 | 0 | 0 | 0 |

TEST EXAMPLE 6

Vats (33 cm×23 cm×11 cm) were filled with upland field soil, and the seeds of wheat, catchweed bedstraw, common chickweed, persian speedwell and field pansy were sowed therein and cultivated for 18 days in a greenhouse. A designated amount of the test compound formulated in an emulsifiable concentrate as in Formulation Example 2 or 5 was diluted with water containing a spreading agent, and the dilution was sprayed over the foliage of the test plants by means of a small hand sprayer at a spray volume of 5 liters per are. The test plants were further grown in the greenhouse for 20 days, and the herbicidal activity was examined. At the time of the application, the test plants were generally at the 1 to 4 leaf stage and in 2 to 12 cm height, although the growing stage of the test plants varied depending on their species. The results are shown in Table 9.

TABLE 9

| Compound No. | Dosage (g/are) | Herbicidal activity | | | | |
|---|---|---|---|---|---|---|
| | | Wheat | Catch-weed bedstraw | Common chick-weed | Persian speed-well | Field pansy |
| 2 | 0.1 | 3 | 10 | 9 | 10 | 10 |
| 3 | 0.1 | 3 | 9 | — | 10 | 10 |
| 4 | 0.1 | 1 | 9 | — | 10 | 10 |
| 6 | 0.1 | 3 | 10 | 0 | 10 | 10 |
| A | 0.1 | 0 | 0 | 0 | 0 | 0 |

TEST EXAMPLE 7

Vats (33 cm×23 cm×11 cm) were filled with upland field soil, and the seeds of barnyardgrass (*Echinochloa crus-galli*), johnsongrass, green foxtail, common cocklebur, tall morningglory, velvetleaf, black nightshade and sicklepod were sowed therein and cultivated for 18 days in a greenhouse. A designated amount of the test compound formulated in an emulsifiable concentrate as in Formulation Example 2 or 5 was diluted with water containing a spreading agent, and the dilution was sprayed over the foliage of the test plants by means of a small hand sprayer at a spray volume of 5 liters per are. The test plants were further grown in the greenhouse for 20 days, and the herbicidal activity was examined. At the time of the application, the test plants were generally at the 1 to 4 leaf stage and in 2 to 12 cm height, although the growing stage of the test plants varied depending on their species. The results are shown in Table 10.

TABLE 10

| Compound No. | Dosage (g/are) | Herbicidal activity | | | | | | | |
|---|---|---|---|---|---|---|---|---|---|
| | | Green foxtail | Barn-yard-grass | Johnson-grass | Common cock-lebur | Tall morning-glory | Velvet-leaf | Black night-shade | Sickle-pod |
| 1 | 0.2 | 10 | 8 | 9 | 10 | 10 | 10 | 10 | 9 |
| 3 | 0.2 | 8 | 7 | 10 | 10 | 10 | 10 | 10 | 10 |
| 5 | 0.2 | 10 | 10 | 10 | 10 | 10 | 10 | 10 | 10 |
| 7 | 0.2 | 8 | — | — | — | 10 | 10 | 10 | 10 |
| 10 | 0.2 | 10 | — | 8 | — | 10 | 10 | 10 | 10 |
| 13 | 0.2 | 0 | 8 | 8 | 10 | 10 | 10 | 10 | 10 |
| A | 0.2 | 0 | 0 | 0 | 0 | 0 | 0 | 0 | 0 |

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

What is claimed is:

1. A compound of the formula:

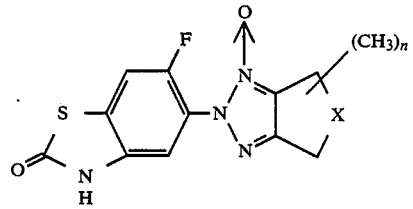

wherein X is a $C_1$-$C_4$ alkylene group which may be substituted with at least one methyl or a —$OCH_2$— group and n is an integer of 0, 1 or 2.

* * * * *